United States Patent
Nojima et al.

(10) Patent No.: US 8,885,949 B2
(45) Date of Patent: Nov. 11, 2014

(54) PATTERN SHAPE DETERMINING METHOD, PATTERN SHAPE VERIFYING METHOD, AND PATTERN CORRECTING METHOD

(75) Inventors: Shigeki Nojima, Kanagawa (JP); Tetsuaki Matsunawa, Kanagawa (JP); Soichi Inoue, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 132 days.

(21) Appl. No.: 13/238,383

(22) Filed: Sep. 21, 2011

(65) Prior Publication Data

US 2012/0076424 A1     Mar. 29, 2012

(30) Foreign Application Priority Data

Sep. 24, 2010   (JP) ................................ 2010-213581

(51) Int. Cl.
*G06K 9/46* (2006.01)
*G03F 7/00* (2006.01)
*G01N 21/00* (2006.01)
*G06K 9/00* (2006.01)

(52) U.S. Cl.
CPC .. *G06K 9/00* (2013.01); *G03F 7/00* (2013.01); *G01N 21/00* (2013.01)
USPC .......................................... 382/203; 382/151

(58) Field of Classification Search
None
See application file for complete search history.

(56) References Cited

U.S. PATENT DOCUMENTS

| | | | |
|---|---|---|---|
| 6,347,150 B1 * | 2/2002 | Hiroi et al. | 382/149 |
| 7,138,629 B2 * | 11/2006 | Noji et al. | 250/311 |
| 7,794,897 B2 | 9/2010 | Kotani | |
| 2003/0162105 A1 * | 8/2003 | Nojima et al. | 430/5 |
| 2004/0257568 A1 * | 12/2004 | Yamane | 356/394 |
| 2005/0250022 A1 * | 11/2005 | Kotani et al. | 430/5 |
| 2008/0022244 A1 * | 1/2008 | Nojima | 716/5 |
| 2008/0250381 A1 * | 10/2008 | Kotani et al. | 716/19 |
| 2009/0053619 A1 * | 2/2009 | Maeda et al. | 430/5 |
| 2009/0202924 A1 * | 8/2009 | Yamamoto et al. | 430/5 |
| 2010/0159709 A1 | 6/2010 | Kotani | |

FOREIGN PATENT DOCUMENTS

| | | |
|---|---|---|
| JP | 2008-041940 | 2/2008 |
| JP | 2008-204144 | 9/2008 |
| JP | 2008-233687 | 10/2008 |
| JP | 2010-034138 | 2/2010 |
| JP | 2011-085616 | 4/2011 |

* cited by examiner

*Primary Examiner* — Atiba O Fitzpatrick
*Assistant Examiner* — Carol Wang
(74) *Attorney, Agent, or Firm* — Finnegan, Henderson, Farabow, Garrett & Dunner, L.L.P.

(57) ABSTRACT

According to the pattern shape determining method of the embodiment, a first reference position of a pattern shape is set on a first pattern and a second reference position of a pattern shape is set on a second pattern. Moreover, an allowable dimensional difference between the first pattern and the second pattern is set to a value corresponding to a distance from the first reference position. Then, it is determined whether the second pattern has a pattern shape identical with the first pattern, based on whether a dimensional difference between the first pattern and the second pattern is within a range of an allowable dimensional difference set at a position at which the dimensional difference is calculated.

17 Claims, 5 Drawing Sheets

DISTANCE FROM POINT OF INTEREST A (nm)

PATTERN SHAPE DETERMINING METHOD, PATTERN SHAPE VERIFYING METHOD, AND PATTERN CORRECTING METHOD

CROSS-REFERENCE TO RELATED APPLICATIONS

This application is based upon and claims the benefit of priority from the prior Japanese Patent Application No. 2010-213581, filed on Sep. 24, 2010; the entire contents of which are incorporated herein by reference.

FIELD

Embodiments described herein relate generally to a pattern shape determining method, a pattern shape verifying method, and a pattern correcting method.

BACKGROUND

Recent progress of a semiconductor manufacturing technology is extremely remarkable, and semiconductor devices with a minimum feature size of 40 nm are mass-produced. Such scaling of semiconductor devices is realized by rapid progress of a micro-patterning technology such as a mask process technology, a photolithography technology, and an etching technology. In the generation in which a pattern size is sufficiently large, a plane shape of an integrated circuit pattern that needs to be formed on a wafer is directly written as a design pattern and a mask pattern faithful to the design pattern is manufactured. Then, the manufactured mask pattern is transferred onto the wafer by projection optics, and a pattern approximately the same as the design pattern is formed on the wafer by etching a base with resist as a processing target film.

However, with the progress of scaling of an integrated circuit pattern, it has become difficult to faithfully form a pattern in each process. Consequently, a problem arises in that final finished dimensions do not become as a design pattern. Specially, in the lithography process or the etching process that is the most important process for achieving micro-patterning, patterns arranged around a pattern that needs to be formed greatly affect the dimensional accuracy of the pattern that needs to be formed.

In order to avoid such influence, technologies, such as the OPC (Optical Proximity Correction) and the PPC (Process Proximity Correction), are developed. In these technologies, an auxiliary pattern is added in advance or a width of a pattern is thickened or thinned so that a shape of a processed integrated circuit pattern becomes a design pattern (desired value).

Moreover, development of an OPC verifying technology has been progressed in which whether a pattern shape after the OPC or the PPC is appropriate is verified by OPC verification using a process simulation such as lithography and processing.

However, the OPC verification performs simulation such as lithography and processing and therefore takes a long time in the case of being performed on the whole integrated circuit pattern. Therefore, identical patterns are extracted from the integrated circuit pattern and the same simulation result is applied to the identical patterns. Thus, it is desired to determine whether a pattern shape is identical between patterns efficiently and accurately.

DETAILED DESCRIPTION

According to a pattern shape determining method of an embodiment, a first reference position to be a determination reference position of a pattern shape is set on a first pattern to be a criterion of a pattern shape and a second reference position to be a determination reference position of a pattern shape is set on a second pattern as a determination target for which it is determined whether a pattern shape is identical with the first pattern. Moreover, an allowable dimensional difference between the first pattern and the second pattern as a criterion used when determining whether the first pattern and the second pattern have an identical shape is set to a value corresponding to a distance from the first reference position for each distance. Then, it is determined whether the second pattern has a pattern shape identical with the first pattern based on whether a dimensional difference between the first pattern and the second pattern calculated for each position from the first reference position and the second reference position is within a range of an allowable dimensional difference set at a position at which the dimensional difference is calculated.

A pattern shape determining method, a pattern shape verifying method, and a pattern correcting method according to the embodiment will be explained below in detail with reference to the accompanying drawings. The present invention is not limited to this embodiment.

Embodiment

Figure 1:
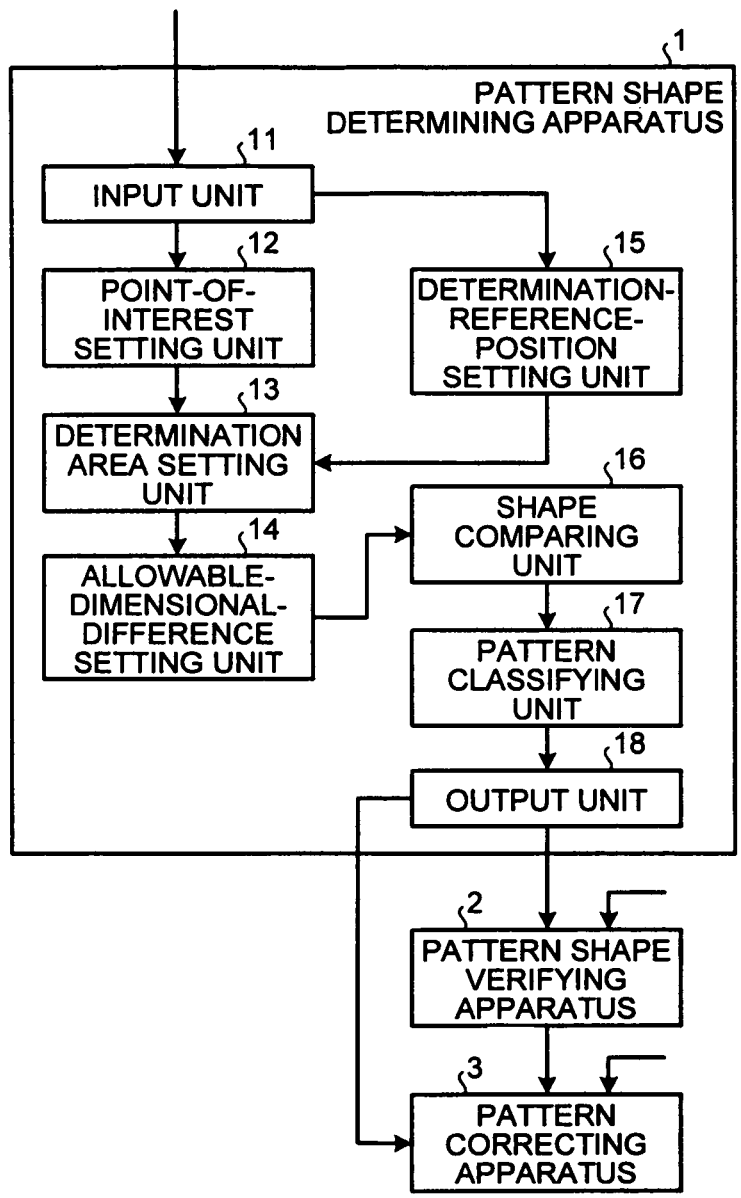
FIG. 1 is a block diagram illustrating a configuration of a pattern shape determining apparatus according to a present embodiment.

FIG. 1 is a block diagram illustrating a configuration of a pattern shape determining apparatus according to the present embodiment. A pattern shape determining apparatus 1 is, for example, a computer that determines whether a first pattern (determination reference pattern Pa to be described later) to be a criterion of a pattern shape and a second pattern (determination target pattern Pb to be described later) to be a determination target of a pattern shape have an identical shape.

In lithography, the effect on a predetermined position (point of interest) on a pattern is larger in a pattern closer to the point of interest and is smaller in a pattern further from the point of interest. Therefore, in the present embodiment, pattern matching considering a distance from a point of interest is performed for analyzing a pattern shape centered on the point of interest.

The pattern shape determining apparatus 1 in the present embodiment sets a point of interest A to be described later at a predetermined position on a design pattern (layout data) of an integrated circuit pattern. Moreover, the pattern shape determining apparatus 1 sets an allowable dimensional difference (dimensional tolerance x to be described later) between the determination reference pattern Pa and the determination target pattern Pb as a criterion value for determining whether the determination reference pattern Pa and the determination target pattern Pb have an identical shape. The pattern shape determining apparatus 1 sets the dimensional tolerance x according to the distance from the point of interest A for each distance from the point of interest A.

The pattern shape determining apparatus 1 determines whether the dimensional difference between the determination reference pattern Pa and the determination target pattern Pb is within the range of the dimensional tolerance x for each distance from the point of interest A based on the dimensional tolerance x. The pattern shape determining apparatus 1 determines the determination target pattern Pb determined to have a dimensional difference within the range of the dimensional tolerance x as a pattern having a shape identical with the determination reference pattern Pa. Moreover, the pattern shape determining apparatus 1 determines the determination target pattern Pb determined to have a dimensional difference not within the range of the dimensional tolerance x as a pattern having a shape different from the determination reference pattern Pa.

The pattern shape determining apparatus 1, for example, determines whether the determination reference pattern Pa and the determination target pattern Pb have an identical shape between a first design pattern and a second design pattern. Put another way, the pattern shape determining apparatus 1 determines whether the determination reference pattern Pa included in the first design pattern and the determination target pattern Pb included in the second design pattern have an identical shape.

The pattern shape determining apparatus 1 can determine whether the determination reference pattern Pa and the determination target pattern Pb have an identical shape in one design pattern such as for one chip or one shot. Moreover, the pattern shape determining apparatus 1 can set a pattern near a hot spot as the determination reference pattern Pa.

The hot spot is a portion in which dimensional variation is large in a pattern formed on a substrate such as a wafer and is a position (coordinates) having a possibility to be a pattern formation failure higher than a predetermined value. In other words, the hot spot is a portion that causes a problem (such as disconnection and short-circuit of a pattern) on a wafer detected in a lithography simulation or the like.

The pattern shape determining apparatus 1 includes an input unit 11, a point-of-interest setting unit 12, a determination area setting unit 13, an allowable-dimensional-difference setting unit 14, a determination-reference-position setting unit 15, a shape comparing unit 16, a pattern classifying unit 17, and an output unit 18.

The first design pattern (for example, for one chip or one shot) in which the point of interest A and the determination reference pattern Pa are set, the second design pattern (for example, for one chip or one shot) in which the determination target pattern Pb is set, and the like are input to the input unit 11. The input unit 11 sends the first design pattern to the point-of-interest setting unit 12 and sends the second design pattern to the determination-reference-position setting unit 15.

The point-of-interest setting unit 12 sets the point of interest A on the first design pattern. The point-of-interest setting unit 12, for example, sets respective positions on the first design pattern to the point of interest A in order with predetermined dimensional intervals. The point-of-interest setting unit 12 can set the position of a minimum dimension on the first design pattern, the hot spot, the position specified by an engineer based on past findings or the like, or the like to the point of interest A. The point-of-interest setting unit 12 sends the coordinates of the point of interest A and the first design pattern to the determination area setting unit 13.

The determination-reference-position setting unit 15 sets the reference position (determination target reference position B) of the determination target pattern Pb on the second design pattern. The determination-reference-position setting unit 15 sets respective positions on the second design pattern to the determination target reference position B in order with predetermined dimensional intervals. The determination-reference-position setting unit 15 sends the coordinates of the determination target reference position B and the second design pattern to the determination area setting unit 13.

The determination area setting unit 13 sets an area (determination area Ja) to be a determination reference (determination target) of a pattern shape around the point of interest A. The determination area Ja is, for example, an area having a predetermined distance range from the point of interest A on the first design pattern. The determination area setting unit 13 sets one to a plurality of the determination areas Ja on the first design pattern, for example, by setting a distance range in a plus X direction, a distance range in a minus X direction, a distance range in a plus Y direction, and a distance range in a minus Y direction from the point of interest A.

Moreover, the determination area setting unit 13 sets an area (determination area Jb) to be a determination target of a pattern shape around the determination target reference position B. The determination area Jb is, for example, an area having a predetermined distance range from the determination target reference position B on the second design pattern. The determination area Ja and the determination area Jb are areas having the same size.

For example, the center coordinates (coordinates of the point of interest A in the determination area Ja) of the determination area Ja and the center coordinates (coordinates of the determination target reference position B in the determination area Jb) of the determination area Jb are the same coordinates. The determination area setting unit 13 associates the determination area Ja and the determination area Jb that are set as areas having the same size with each other and generates information (information indicating a set of the determination areas Ja and Jb associated for each size of an area) indicating the association, and sends the information to the allowable-dimensional-difference setting unit 14.

The determination area setting unit 13 sends the coordinates (ranges) of the determination areas Ja on the first design pattern and the first design pattern to the allowable-dimensional-difference setting unit 14. Moreover, the determination area setting unit 13 sends the coordinates (ranges) of the determination areas Jb on the second design pattern and the second design pattern to the allowable-dimensional-difference setting unit 14.

The allowable-dimensional-difference setting unit 14 sets the dimensional tolerance x between the determination reference pattern Pa and the determination target pattern Pb for each set of the determination areas Ja and Jb. The dimensional tolerance x is a criterion for determining whether the determination reference pattern Pa and the determination target pattern Pb have an identical shape. The allowable-dimensional-difference setting unit 14 sets the dimensional tolerance x for each set of the determination areas Ja and Jb based on the distance from the point of interest A of each determination area Ja. Consequently, the dimensional tolerance x according to the distance from the point of interest A is set for each set of the determination areas Ja and Jb.

The allowable-dimensional-difference setting unit 14 sets the dimensional tolerance x, for example, based on the dimensional tolerance (reference value for determining whether or not the determination areas Ja and Jb have an identical shape) between on-wafer pattern dimensions when the determination reference pattern Pa is formed on a wafer and on-wafer pattern dimensions when the determination target pattern Pb is formed on a wafer. The allowable-dimensional-difference setting unit 14 can set the dimensional tolerance x based on minimum pattern dimensions in the determination target pattern Pb. The dimensional tolerance x is set to, for example, a dimension that is 5% or less of the minimum pattern dimensions of the determination reference pattern Pa or the determination target pattern Pb. The allowable-dimensional-difference setting unit 14 sends a set of the set dimensional tolerance x, the determination area Ja, and the determination area Jb to the shape comparing unit 16.

The shape comparing unit 16 determines whether the determination reference pattern Pa and the determination target pattern Pb have an identical shape based on the dimensional tolerance x for each set of the determination areas Ja and Jb. For example, when the dimensional difference between the pattern dimensions of the determination reference pattern Pa in the determination area Ja and the pattern dimensions of the determination target pattern Pb in the determination area Jb is within the range of the dimensional tolerance x, the shape comparing unit 16 determines that the determination reference pattern Pa and the determination target pattern Pb have an identical shape. The shape comparing unit 16 sends the result of shape determination, the determination reference patterns Pa, and the determination target patterns Pb to the pattern classifying unit 17.

The pattern classifying unit 17 associates the determination target patterns Pb that are each determined to have a shape identical with the determination reference pattern Pa among the determination target patterns Pb with each other, as an identical shape group. Moreover, the pattern classifying unit 17 associates the determination target patterns Pb that are each determined to have a shape different from the determination reference pattern Pa among the determination target patterns Pb with each other, as a non-identical shape group. The pattern classifying unit 17 sends the determination target patterns Pb set in the identical shape group and the determination target patterns Pb set in the non-identical shape group to the output unit 18.

The output unit 18 sends each of the determination target patterns Pb set in the identical shape group and the determination target patterns Pb set in the non-identical shape group to a pattern shape verifying apparatus 2 or a pattern correcting apparatus 3.

The pattern shape verifying apparatus 2 is an apparatus that derives the shape of an on-wafer pattern (resist pattern or etched pattern), for example, by applying the OPC and the lithography simulation to the second design pattern. The OPC to the second design pattern can be performed by the pattern correcting apparatus 3. The pattern shape verifying apparatus 2 sets an identical on-wafer pattern (for example, on-wafer pattern of the determination reference pattern Pa) with respect to the determination target pattern Pb set in the identical shape group. The pattern shape verifying apparatus 2 verifies the derived shape of the on-wafer pattern by comparing the shape of the on-wafer pattern with the second design pattern. The pattern shape verifying apparatus 2 sends the shape verification result of the on-wafer pattern to the pattern correcting apparatus 3.

The pattern correcting apparatus 3 generates a mask pattern (correction pattern) by performing the OPC on the second design pattern based on the shape verification result of the on-wafer pattern. The pattern correcting apparatus 3 applies an identical mask pattern to the determination target pattern Pb set in the identical shape group. The pattern correcting apparatus 3 can correct a mask-pattern based on the determination target patterns Pb set in the identical shape group and the determination target patterns Pb set in the non-identical shape group. In this case, the pattern correcting apparatus 3 corrects a mask pattern by using a correction pattern library to be described later.

Figure 2:
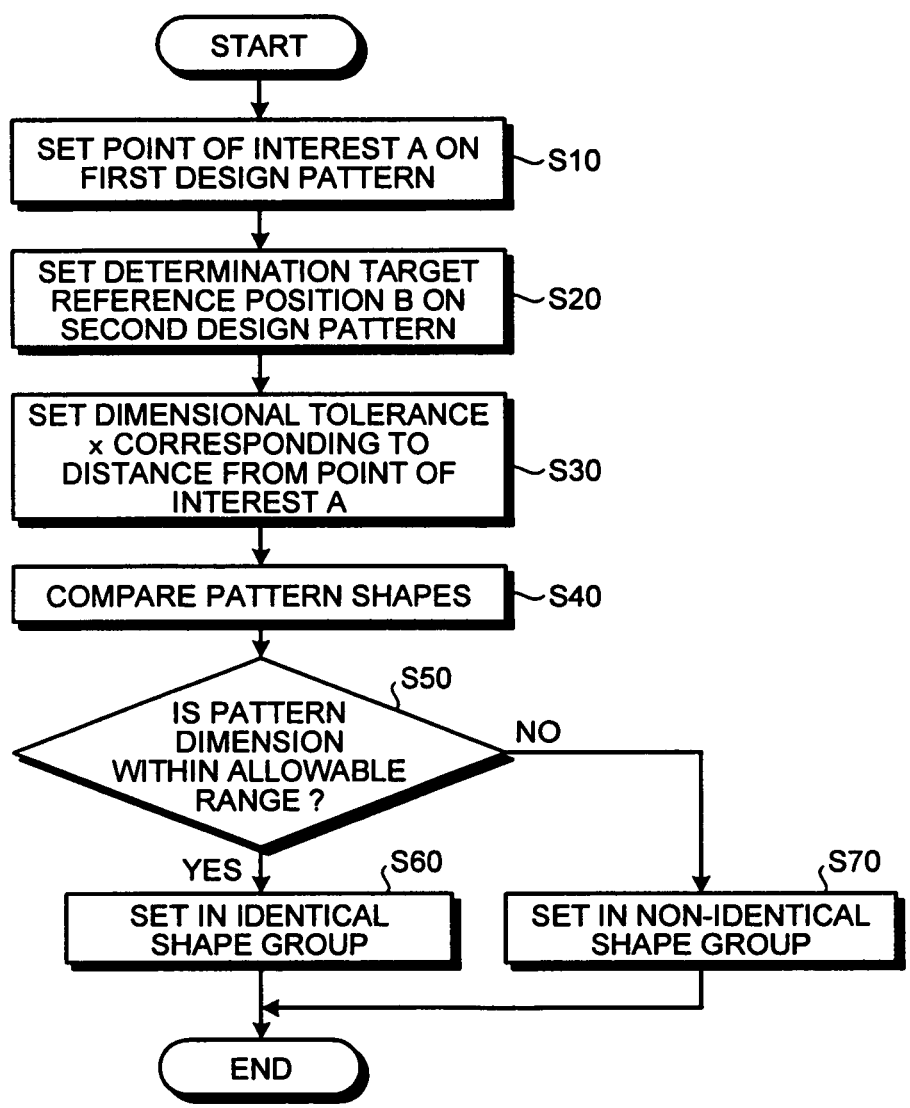
FIG. 2 is a flowchart illustrating a process procedure of a pattern shape determining process.

Next, the process procedure of the pattern shape determining process is explained. FIG. 2 is a flowchart illustrating the process procedure of the pattern shape determining process. The first design pattern in which the determination reference patterns Pa are set, the second design pattern in which the determination target patterns Pb are set, and the like are input to the input unit 11 of the pattern shape determining apparatus 1. The input unit 11 sends the first design pattern to the point-of-interest setting unit 12 and sends the second design pattern to the determination-reference-position setting unit 15.

The point-of-interest setting unit 12 sets the point of interest A on the first design pattern (Step S10). The point-of-interest setting unit 12, for example, sets the hot spot on the first design pattern as the point of interest A. The point-of-interest setting unit 12 sends the coordinates of the point of interest A and the first design pattern to the determination area setting unit 13.

Moreover, the determination-reference-position setting unit 15 sets the determination target reference position B on the second design pattern (Step S20). The determination-reference-position setting unit 15 sets respective positions on the second design pattern to the determination target reference position B in order with predetermined dimensional intervals. The determination-reference-position setting unit 15 sends the coordinates of the determination target reference position B and the second design pattern to the determination area setting unit 13.

The determination area setting unit 13 sets one to a plurality of the determination areas Ja to be determination reference of a pattern shape around the point of interest A. Moreover, the determination area setting unit 13 sets the determination areas Jb to be determination targets of a pattern shape around the determination target reference position B. The determination area setting unit 13 sets the determination area Jb having the same size as the determination area Ja with respect to the point of interest A.

Figure 3A:
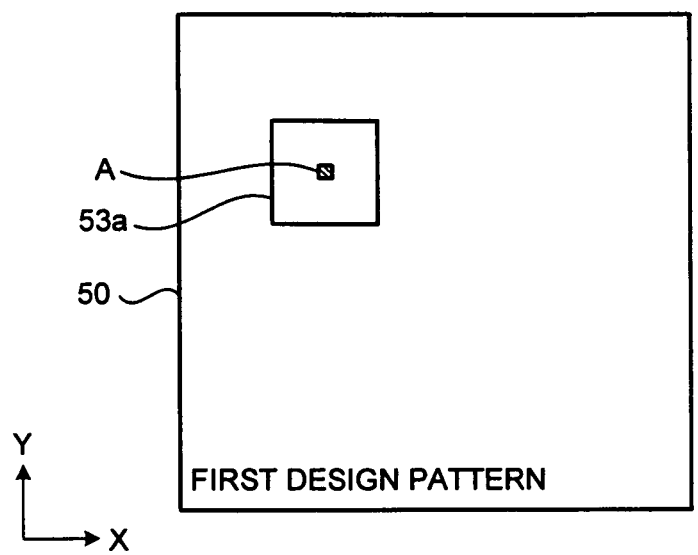
FIG. 3A and FIG. 3B are diagrams for explaining determination areas.
Figure 3B:
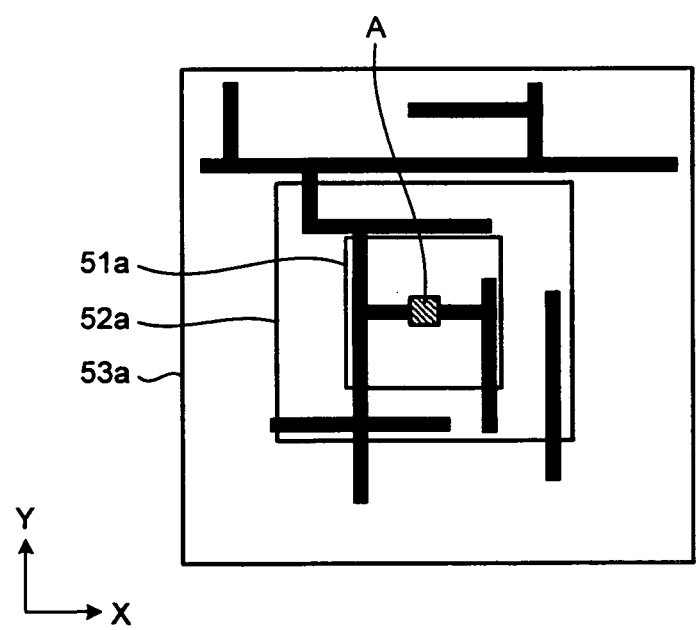

The determination areas Ja and Jb are explained. Because the determination area Ja and the determination area Jb are similar areas, only the determination area Ja is explained. FIG. 3A and FIG. 3B are diagrams for explaining the determination areas. FIG. 3A illustrates a top view of a first design pattern 50 and FIG. 3B illustrates a top view of the determination area Ja.

As shown in FIG. 3A, the point of interest A is set to a position on the first design pattern 50. As shown in FIG. 3B, the determination area setting unit 13 sets a determination area 51a, a determination area 52a, a determination area 53a, and the like as the determination areas Ja around the point of interest A. For example, the determination area 51a is a square area centered on the point of interest A. The determination area 52a is a ring-shaped area surrounding the perimeter of the determination area 51a, and the outer perimeter of the determination area 52a forms a square. The determination area 53a is a ring-shaped area surrounding the perimeter of the determination area 52a, and the outer perimeter of the determination area 53a forms a square.

The determination area 51a is, for example, a square area (range of 75 nm in vertical and horizontal directions from the point of interest A) having a width of 150 nm in an x-axis direction and a Y-axis direction. The determination area 52a is, for example, an area obtained by cutting out the determination area 51a from a square area (range of 350 nm in vertical and horizontal directions from the point of interest A) having a width of 700 nm in the x-axis direction and the Y-axis direction. The determination area 53a is, for example, an area obtained by cutting out the determination areas 51a and 52a from a square area (range of 2500 nm in vertical and horizontal directions from the point of interest A) having a width of 5 µm in the x-axis direction and the Y-axis direction.

The determination area setting unit 13 sets determination areas 51b to 53b (not shown) as the determination areas Jb having the same sizes as the determination areas 51a to 53a on the second design pattern. The determination area setting unit 13 associates the determination area 51a and the determination area 51b that are set as areas having the same size with each other. In the similar manner, the determination area setting unit 13 associates the determination area 52a and the determination area 52b with each other and associates the determination area 53a and the determination area 53b with each other. The determination area setting unit 13 generates information indicating each of the associations of the determination areas 51a and 51b, the determination areas 52a and 52b, and the determination areas 53a and 53b and sends the information to the allowable-dimensional-difference setting unit 14.

A plurality of sets of the determination areas 51a to 53a is set on the first design pattern 50 and a plurality of sets of the determination areas 51b to 53b is set on the second design pattern. It is applicable that each set of the determination areas 51a to 53a set on the first design pattern 50 overlaps an adjacent different set of the determination areas 51a to 53a in part of the areas. In the similar manner, it is applicable that each set of the determination areas 51b to 53b set on the second design pattern overlaps an adjacent different set of the determination areas 51b to 53b in part of the areas.

The determination area setting unit 13 sends the coordinates of the determination areas 51a to 53a on the first design pattern 50 and the first design pattern 50 to the allowable-dimensional-difference setting unit 14. Moreover, the determination area setting unit 13 sends the coordinates of the determination areas 51b to 53b on the second design pattern and the second design pattern to the allowable-dimensional-difference setting unit 14.

The allowable-dimensional-difference setting unit 14 sets the dimensional tolerances x corresponding to the distance from the point of interest A (Step S30). Specifically, the allowable-dimensional-difference setting unit 14 sets the dimensional tolerance x between the determination reference pattern Pa and the determination target pattern Pb for each set of the determination areas Ja and Jb. In other words, the dimensional tolerance x is associated with each set of the determination areas Ja and Jb. The dimensional tolerances x corresponding to the distance from the point of interest A can be derived in advance.

For example, the allowable-dimensional-difference setting unit 14 sets the dimensional tolerance x to zero (no tolerance) with respect to a set of the determination areas 51a and 51b. Moreover, the allowable-dimensional-difference setting unit 14, for example, sets the dimensional tolerance x to 1 nm with respect to a set of the determination areas 52a and 52b and sets the dimensional tolerance x to 5 nm with respect to a set of the determination areas 53a and 53b. The allowable-dimensional-difference setting unit 14 sends a set of the set dimensional tolerance x and the determination areas Ja and Jb to the shape comparing unit 16.

The shape comparing unit 16 compares the pattern shapes of the determination reference pattern Pa and the determination target pattern Pb based on the dimensional tolerance x for each set of the determination areas Ja and Jb (Step S40). At this time, the shape comparing unit 16 determines whether each of the dimensional differences between the pattern dimensions of the determination reference patterns Pa at the first to the N-th (N is a natural number) coordinates in the determination area Ja and the pattern dimensions of the determination target patterns Pb at the first to the N-th coordinates in the determination area Jb is within the dimensional tolerance x (within the allowable range). Based on this determination result, the shape comparing unit 16 determines whether the determination reference pattern Pa and the determination target pattern Pb have an identical shape for each set of the determination areas 51a and 51b to the determination areas 53a and 53b.

For example, when the dimensional difference at the same coordinates between the pattern dimensions of the determination reference pattern Pa in the determination area 51a and the pattern dimensions of the determination target pattern Pb in the determination area 51b is zero (same dimensions), the determination reference pattern Pa and the determination target pattern Pb are determined to have an identical shape in the determination areas 51a and 51b.

In the similar manner, when the dimensional difference at the same coordinates between the pattern dimensions of the determination reference pattern Pa in the determination area 52a and the pattern dimensions of the determination target pattern Pb in the determination area 52b is 1 nm or less, the determination reference pattern Pa and the determination target pattern Pb are determined to have an identical shape in the determination areas 52a and 52b.

Moreover, when the dimensional difference at the same coordinates between the pattern dimensions of the determination reference pattern Pa in the determination area 53a and the pattern dimensions of the determination target pattern Pb in the determination area 53b is 5 nm or less, the determination reference-pattern Pa and the determination target pattern Pb are determined to have an identical shape in the determination areas 53a and 53b. The shape comparing unit 16 sends the result of the shape determination, the determination reference patterns Pa, and the determination target patterns Pb to the pattern classifying unit 17.

When the shape comparing unit 16 determines that the dimensional difference between the pattern dimensions of the determination reference pattern Pa and the pattern dimensions of the determination target pattern Pb is within the allowable range (Yes at Step S50), the pattern classifying unit 17 sets the determination target pattern Pb determined to have a dimensional difference within the allowable range in the identical shape group (Step S60).

On the other hand, when the shape comparing unit 16 determines that the dimensional difference between the pattern dimensions of the determination reference pattern Pa and the pattern dimensions of the determination target pattern Pb is not within the allowable range (No at Step S50), the pattern classifying unit 17 sets the determination target pattern Pb determined to have a dimensional difference not within the allowable range in the non-identical shape group (Step S70).

The pattern classifying unit 17 sends the determination target patterns Pb set in the identical shape group, the determination target patterns Pb set in the non-identical shape group, and the determination reference patterns Pa to the output unit 18. The output unit 18 sends each of the determination target patterns Pb set in the identical shape group, the determination target patterns Pb set in the non-identical shape group, and the determination reference patterns Pa to the pattern shape verifying apparatus 2 or the pattern correcting apparatus 3.

Thereafter, the pattern shape verifying apparatus 2 verifies the shape of an on-wafer pattern based on the second design pattern. At this time, the pattern shape verifying apparatus 2 applies an identical on-wafer pattern to the determination target pattern Pb set in the identical shape group to omit a shape deriving process for overlapping on-wafer patterns. The pattern shape verifying apparatus 2 sends the verification result to the pattern correcting apparatus 3.

Then, the pattern correcting apparatus 3 corrects the second design pattern based on the shape verification result of on-wafer patterns. At this time, the pattern correcting apparatus 3 applies an identical correction pattern to the determination target pattern Pb set in the identical shape group to omit a calculation process for overlapping correction patterns.

Figure 4:
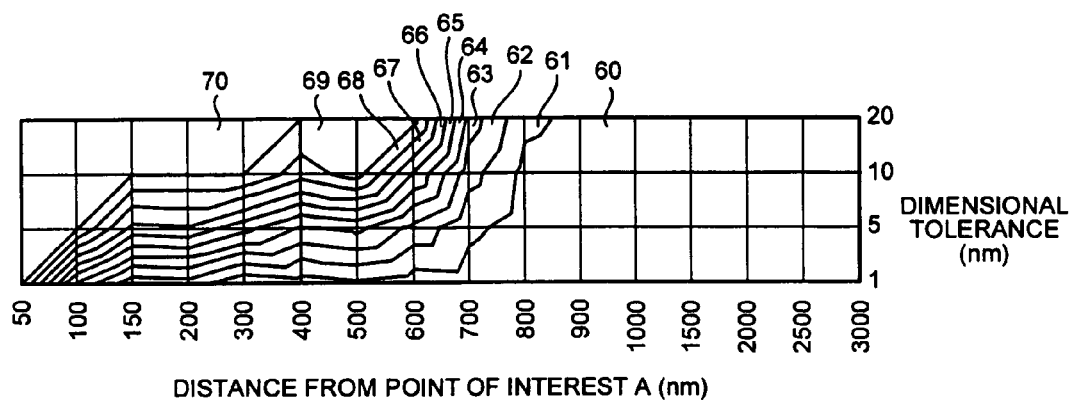
FIG. 4 is a diagram illustrating a relationship between a pattern shape determination condition and an on-wafer dimensional variation amount.

Next, explanation is made for a maximum variation amount (hereinafter, on-wafer dimensional variation amount) of on-wafer dimensions from the ideal value in the case where the pattern shape determining apparatus 1 determines that the determination reference pattern Pa and the determination target pattern Pb have an identical shape. FIG. 4 is a diagram illustrating a relationship between a pattern shape determination condition and the on-wafer dimensional variation amount. In FIG. 4, a horizontal axis indicates a distance from the point of interest A and a vertical axis indicates the dimensional tolerance x.

A variation amount area 60 of the on-wafer dimensional variation amount is an area in which a deviation amount of on-wafer dimensions from the ideal value is 0 to 1 nm. In the similar manner, the variation amount areas 61 to 65 are areas in which a deviation amount of on-wafer dimensions from the ideal value is 1 nm to 2 nm, 2 nm to 3 nm, 3 nm to 4 nm, 4 nm to 5 nm, and 5 nm to 6 nm, respectively. Moreover, the variation amount areas 66 to 70 are areas in which a deviation amount of on-wafer dimensions from the ideal value is 6 nm to 7 nm, 7 nm to 8 nm, 8 nm to 9 nm, 9 nm to 10 nm, and 10 nm to 11 nm, respectively.

In this example, when the dimensional tolerance x from the determination reference pattern Pa in the determination area 51a set around the point of interest A is zero (perfect matching of patterns), the pattern shapes are determined to be identical. Moreover, it is determined whether the pattern shapes are identical while changing the dimensional tolerance x from the determination reference pattern Pa arranged in the determination area 52a or the like to 1 nm, 5 nm, 10 nm, and 20 nm. Furthermore, the width in the X-axis direction and the width in the Y-axis direction of the determination area 52a are changed between 50 nm to 3000 nm.

In such a pattern shape determination condition, the lithography simulation is performed on the determination target pattern Pb determined to have a shape identical with the determination reference pattern Pa by using the pattern shape verifying apparatus 2. In this example, the pattern shape verifying apparatus 2 calculates the on-wafer dimensional variation amount of the determination target pattern Pb determined to have a shape identical with the determination reference pattern Pa.

The pattern shape verifying apparatus 2 calculates the on-wafer dimensional variation amount of the determination target pattern Pb, for example, by using an exposure condition (λ=193 nm, NA=1.20) used when transferring the determination target pattern Pb onto a wafer.

For example, the width in the X-axis direction and the width in the Y-axis direction of the determination area 52a are set to 700 nm. Then, the dimensional tolerance x in the determination area 51a is set to zero and the dimensional tolerance x in the determination area 52a is set to 5 nm. In this case, as shown in FIG. 4, the on-wafer dimensional variation amount (effect on the point of interest A) is at most 2 nm.

In this manner, when the relationship between the pattern shape determination condition and the on-wafer dimensional variation amount as shown in FIG. 4 is determined in advance, derivation of the on-wafer dimensional variation amount of the determination target pattern Pb and setting of the dimensional tolerance x can be performed by using this relationship.

Moreover, the pattern shape verifying apparatus 2 can calculate the effect (on-wafer dimensional variation amount) on the point of interest A by using a predetermined function. The on-wafer dimensional variation amount at the point of interest A can be calculated by using the equation (1) shown below.

$$F(X_1, X_2) = aX_1 \times \left(\frac{2 \times J_1(X_2)}{X_2}\right)^2 + b \qquad (1)$$

where $X_1$ is the dimensional tolerance x and $X_2$ is a distance from the point of interest A. Moreover, $J_1$ is a first order Bessel function, and a and b are coefficients calculated by using a least-squares method. For example, in the case of the graph shown in FIG. 4, $a=1.58\times10^6$ and $b=1.98$. $F(X_1, X_2)$ is the on-wafer-dimensional variation amount.

For example, the dimensional tolerance x in the determination area Ja in which the distance from the point of interest A in vertical and horizontal directions is 150 nm is set to zero. Moreover, the dimensional tolerance x in the determination area Ja in which the distance from the point of interest A in vertical and horizontal directions is 150 nm to 700 nm is set to 1 nm and the dimensional tolerance x in the determination area Ja in which the distance from the point of interest A in vertical and horizontal directions is 700 nm is set to 5 nm. In this case, when the on-wafer dimensional variation amount is calculated by performing the lithography simulation on the determination target pattern Pb determined to have a shape identical with the determination reference pattern Pa, it is found that the on-wafer dimensional variation amount at the point of interest A is less than 2 nm.

Next, explanation is made for the difference between the determination result when pattern determination is performed by the pattern shape determining method according to the present embodiment and the determination result when pattern determination is performed by using a different method. Determination of a pattern shape is performed by various methods (1) to (3) with respect to 31 design patterns that are found in advance that the on-wafer-dimensional variation amount at the point of interest A is 2 nm or less.

Method (1)

When pattern shapes are determined to be identical in the case where pattern shapes in shape determination images of the design patterns perfectly match, it is determined that there are seven pattern variations (seven pattern shapes) in the 31 design patterns.

Method (2)

When pattern shapes are determined to be identical in the case where pattern shapes in shape determination images of the design patterns have a dimensional difference of 1 nm or less or less than 1 nm, it is determined that there are four pattern variations in the 31 design patterns.

Method (3)

When determination of a pattern shape is performed by the pattern shape determining method according to the present embodiment, it is determined that there is only one pattern variation (all of patterns have an identical shape) in the 31 design patterns. In this manner, when determination of a pattern shape is performed while considering the effect on the point of interest A, 31 patterns are verified by verifying one pattern shape as representative, so that the time for pattern verification can be reduced significantly.

Figure 5:
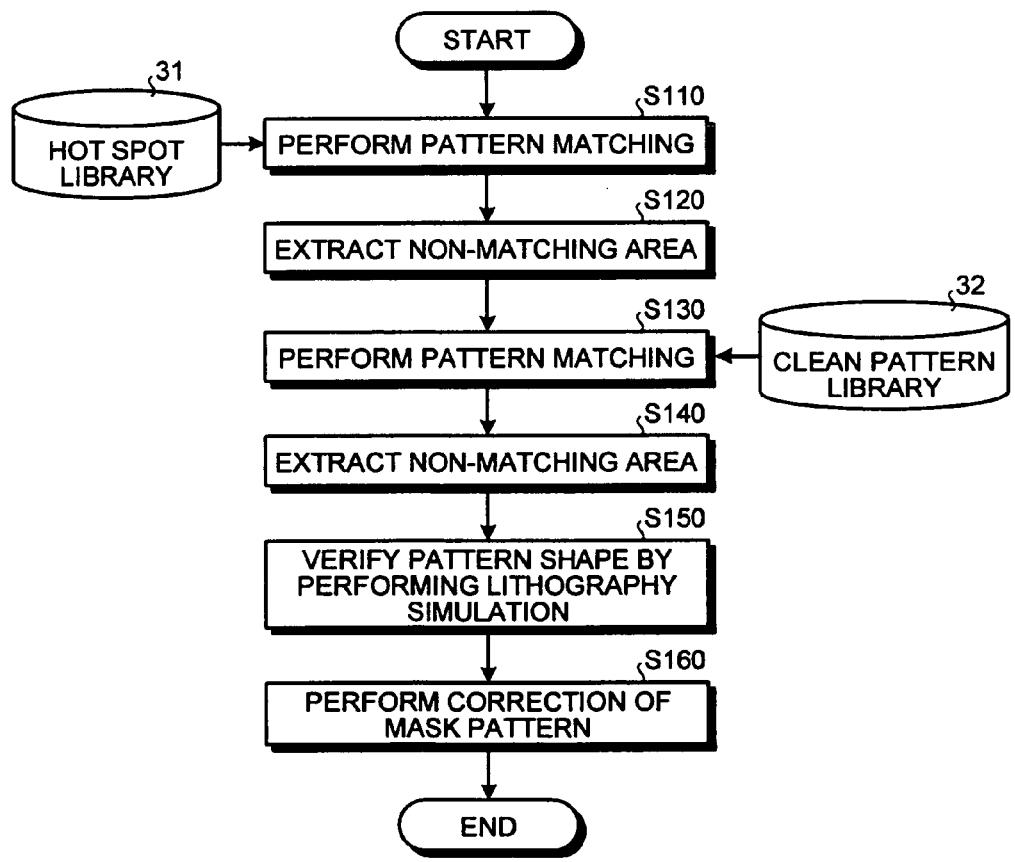
FIG. 5 is a flowchart illustrating a verification process procedure when a pattern shape verifying method according to the present embodiment is applied to a verification process of a design pattern.

Next, explanation is made for the verification process procedure when the pattern shape determining method according to the present embodiment is applied to the verification process of a design pattern. FIG. 5 is a flowchart illustrating the verification process procedure when the pattern shape verifying method according to the present embodiment is applied to the verification process of a design pattern. The second design pattern (GDS data), which is a determination target for a pattern shape and a verification target for a pattern shape, is input to the pattern shape verifying apparatus 2.

The pattern shape verifying apparatus 2 is connected to a hot spot library 31 in which various hot spots are stored. The hot spot library 31 is a storing unit, such as database, that stores findings (pattern shape including a hot spot) found from a lithography simulation, a process simulation, a result of an actually-formed on-wafer pattern, and the like. The hot spot is a pattern having a possibility to be a pattern formation failure higher than a predetermined value when being pattern-transferred onto a wafer.

The hot spots are input to the pattern shape verifying apparatus 2 from the hot spot library 31. The pattern shape verifying apparatus 2 extracts patterns having the same pattern shape as the hot spots from the second design pattern. Specifically, shape comparison (pattern matching) of the determination reference pattern Pa and the determination target pattern Pb is performed with the hot spot as the determination reference pattern Pa (Step S110). In other words, the point of interest A is set on a pattern including the hot spot and the determination target reference position B is set on the second design pattern. Then, shape comparison of the determination reference pattern Pa and the determination target pattern Pb is performed centered on the point of interest A and the determination target reference position B. The pattern shape verifying apparatus 2 extracts an area that does not match the hot spot from the second design pattern (Step S120).

The pattern shape verifying apparatus 2 is connected to a clean pattern library 32 that stores various clean patterns. The clean pattern library 32 is a storing unit, such as database, that stores findings (pattern shape including a clean pattern) found from a lithography simulation, a process simulation, a result of an actually-formed on-wafer pattern, and the like. The clean pattern is a pattern that is found not to become the hot spot and is a pattern that does not need pattern verification. In other words, the clean pattern is a pattern having a possibility to be a pattern formation failure lower than a predetermined value when being pattern-transferred onto a wafer. The clean patterns are input to the pattern shape verifying apparatus 2 from the clean pattern library 32.

The pattern shape verifying apparatus 2 extracts patterns having the same pattern shape as the clean patterns from the second design pattern. Specifically, shape comparison (pattern matching) of the determination reference pattern Pa and the determination target pattern Pb is performed with the clean pattern as the determination reference pattern Pa (Step S130). In other words, the point of interest A is set on a pattern including the clean pattern and the determination target reference position B is set on the second design pattern. Then, shape comparison of the determination reference pattern Pa and the determination target pattern Pb is performed centered on the point of interest A and the determination target reference position B. The pattern shape verifying apparatus 2 extracts an area that does not match the clean pattern from the second design pattern (Step S140).

Consequently, an area that does not match either the hot spot or the clean pattern is extracted from the second design pattern as a verification target pattern. It is applicable that the pattern shape verifying apparatus 2 performs pattern matching with the clean pattern first and thereafter performs pattern matching with the hot spot.

In terms of a pattern finally remained as the verification target pattern, an on-wafer pattern and the like are unknown. Therefore, the lithography simulation and the like are performed on the verification target pattern and the presence or absence of a problematic portion (pattern that needs to be corrected) and the like are analyzed.

Specifically, the pattern shape verifying apparatus 2 performs the OPC on the verification target pattern and performs the lithography simulation on the verification target pattern after the OPC, thereby deriving the shape of an on-wafer pattern. The pattern shape verifying apparatus 2 verifies the derived shape of the on-wafer pattern by comparing the shape of the on-wafer pattern with the second design pattern (Step S150). The pattern shape verifying apparatus 2 sends the shape verification result of the on-wafer pattern to the pattern correcting apparatus 3.

The pattern correcting apparatus 3 corrects the verification target pattern based on the shape verification result of the on-wafer pattern (Step S160). Moreover, the pattern correcting apparatus 3 corrects a design pattern of the hot spot. At this time, the pattern correcting apparatus 3 applies an identical correction pattern to the host spot set in the identical shape group to omit a calculation process for overlapping correction patterns.

Moreover, the pattern correcting apparatus 3 corrects a design pattern of the clean pattern. At this time, the pattern correcting apparatus 3 applies an identical correction pattern to the clean pattern set in the identical shape group to omit a calculation process for overlapping correction patterns.

In this manner, in the present embodiment, it is checked whether the second design pattern matches the hot spot or the clean pattern in advance and analysis on a pattern area that matches the hot spot or the clean pattern is omitted. Therefore, a pattern area on which analysis is actually performed by simulation or the like becomes narrower than the whole area of the second design pattern. Thus, an analysis TAT (verification TAT) can be shortened.

Figure 6:
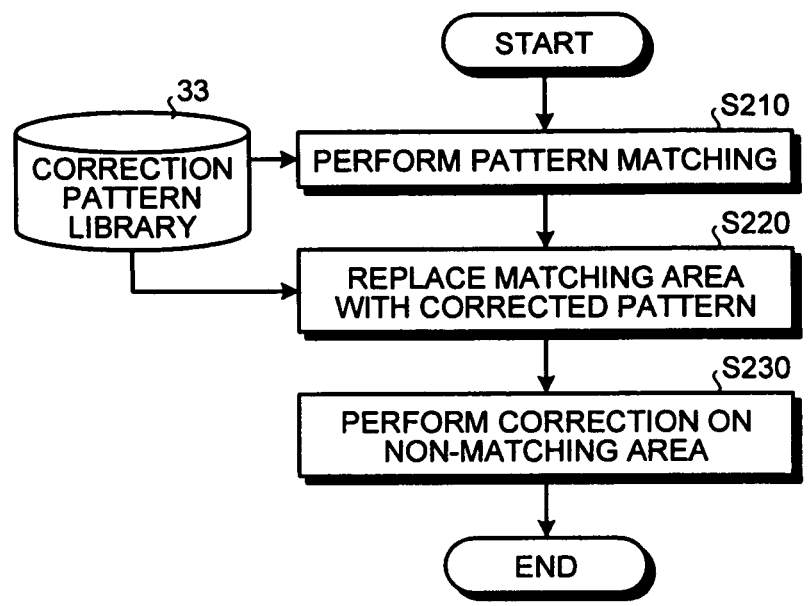
FIG. 6 is a flowchart illustrating an optical-proximity-correction process procedure when the pattern shape verifying method according to the present embodiment is applied to an optical proximity correction.

Moreover, the pattern shape verifying method according to the present embodiment can be applied to the optical proximity correction (OPC) of the second design pattern. FIG. 6 is a flowchart illustrating an optical-proximity-correction process procedure when the pattern shape verifying method according to the present embodiment is applied to the optical proximity correction. The pattern shape determining apparatus 1 and the pattern correcting apparatus 3 are connected to a correction pattern library 33 that stores various correction patterns.

The correction pattern library 33 is a storing unit, such as database, that stores the first design pattern (one to a plurality of the determination reference patterns Pa) for performing shape comparison with the second design pattern (determination target patterns Pb) and a mask pattern (corrected pattern) obtained by performing the OPC on each determination reference pattern Pa. In the correction pattern library 33, the determination reference pattern Pa and a corrected pattern that is the determination reference pattern Pa after correction are associated with each other.

The determination reference patterns Pa are input from the correction pattern library 33 to the pattern shape determining apparatus 1. Moreover, the second design pattern in which the determination target patterns Pb are set and the like are input to the pattern shape determining apparatus 1.

The pattern shape determining apparatus 1 performs shape comparison (pattern matching) of the determination reference pattern Pa and the determination target pattern Pb (Step S210). The pattern shape determining apparatus 1 extracts the determination target pattern Pb that matches the determination reference pattern Pa in shape from the second design pattern based on the result of the pattern matching.

The pattern shape determining apparatus 1 sends the extracted determination target pattern Pb to the pattern correcting apparatus 3. The pattern correcting apparatus 3 reads out the corrected pattern of the determination reference pattern Pa corresponding to the determination target pattern Pb extracted by the pattern shape determining apparatus 1 from the correction pattern library 33. The pattern correcting apparatus 3 applies the read-out corrected pattern to the mask pattern of the determination target pattern Pb. In other words, the pattern correcting apparatus 3 replaces an area matching the determination reference pattern Pa with a corrected pattern (Step S220).

Furthermore, the pattern correcting apparatus 3 corrects a design pattern to a mask pattern with respect to an area that does not match the determination reference pattern Pa by using a rule model or a model base (simulation model) (Step S230). Thereafter, a mask pattern corresponding to the second design pattern is output from the pattern correcting apparatus 3.

Consequently, an area on which correction from a design pattern to a mask pattern is performed becomes narrower than the case of correcting the whole second design pattern. Thus, a correction TAT can be shortened.

The determination process of a pattern shape is performed for example, for each layer in a wafer process. Then, a mask pattern is generated by correcting a design pattern and a mask (photomask) (lithography mask) is manufactured by using the mask pattern. Moreover, a semiconductor device (semiconductor integrated circuit) is manufactured by using the manufactured mask. Specifically, exposure is performed on a wafer to which resist is applied by using the mask, and thereafter the wafer is developed to form a resist pattern on the wafer. Then, the lower layer side of the resist pattern is etched with the resist pattern as a mask. Consequently, an actual pattern is formed on the wafer. When manufacturing a semiconductor device, the above-described determination of a pattern shape, generation of a mask pattern, manufacturing of a mask, exposure process, development process, etching process, and the like are performed for each layer.

Figure 7:
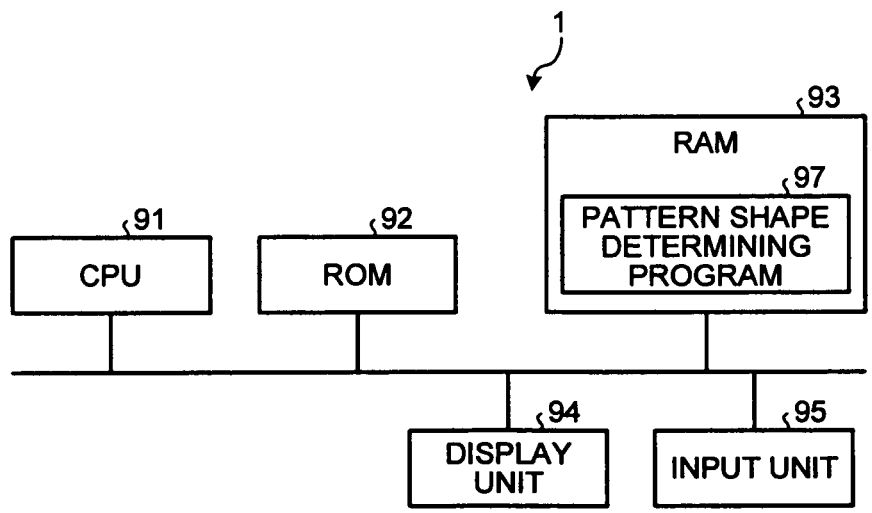
FIG. 7 is a diagram illustrating the hardware configuration of the pattern shape determining apparatus.

Next, the hardware configuration of the pattern shape determining apparatus 1 is explained. FIG. 7 is a diagram illustrating the hardware configuration of the pattern shape determining apparatus. The pattern shape determining apparatus 1 includes a CPU (Central Processing Unit) 91, a ROM (Read Only Memory) 92, a RAM (Random Access Memory) 93, a display unit 94, and an input unit 95. In the pattern shape determining apparatus 1, the CPU 91, the ROM 92, the RAM 93, the display unit 94, and the input unit 95 are connected via a bus line.

The CPU 91 executes determination of a pattern by using a pattern shape determining program 97 that is a computer program. The display unit 94 is a display apparatus such as a liquid crystal monitor, and displays the first design pattern, the second design pattern, the determination areas Ja and Jb, the determination reference pattern Pa, the determination target pattern Pb, the point of interest A, the determination target reference position B, the dimensional tolerance x, the determination result of whether pattern shapes are identical, and the like based on an instruction from the CPU 91. The input unit 95 is configured to include a mouse and a keyboard, and inputs instruction information (such as parameter necessary for determination of a pattern shape) that is externally input by a user. The instruction information input to the input unit 95 is sent to the CPU 91.

The pattern shape determining program 97 is stored in the ROM 92 and is loaded in the RAM 93 via the bus line. FIG. 7 illustrates a state where the pattern shape determining program 97 is loaded in the RAM 93.

The CPU 91 executes the pattern shape determining program 97 loaded in the RAM 93. Specifically, in the pattern shape determining apparatus 1, the CPU 91 reads out the pattern shape determining program 97 from the ROM 92, loads it in a program storage area in the RAM 93, and executes various processes, in accordance with the input of an instruction by a user from the input unit 95. The CPU 91 temporarily stores various data generated in the various processes in the data storage area formed in the RAM 93.

The pattern shape determining program 97 executed in the pattern shape determining apparatus 1 has a module configuration including the point-of-interest setting unit 12, the determination area setting unit 13, the allowable-dimensional-difference setting unit 14, the determination-reference-position setting unit 15, the shape comparing unit 16, and the pattern classifying unit 17, which are loaded in a main storage device to be generated on the main storage device.

In the present embodiment, pattern verification is simplified by using two libraries, i.e., the hot spot library 31 and the clean pattern library 32, however, pattern verification can be simplified by using any one of the two libraries.

Moreover, in the present embodiment, it is determined whether pattern shapes are identical with respect to a design pattern, however, it is applicable to perform determination of whether pattern shapes are identical with respect to a mask pattern.

Furthermore, the determination areas Ja and Jb are not limited to a square area and can be an area having other shapes (for example, a circular area and a rectangular area). Moreover, the dimensional tolerance x for each of the determination areas Ja and Jb can be set by using the function expressed by equation (1).

Moreover, the pattern shape determining method according to the present embodiment is not limited to light exposure of $\lambda=193$ nm and can be applied to EUV (Extreme Ultra-Violet).

In this manner, according to the present embodiment, it is determined whether the determination reference pattern Pa and the determination target pattern Pb have an identical shape based on the dimensional tolerance x set according to the distance from the point of interest A, so that it becomes possible to determine whether pattern shapes are identical between patterns efficiently and accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of determining a pattern shape, comprising:
setting, by a computer, as a point-of-interest position, a first reference position associated with a first pattern;
setting, by a computer, as a determination reference position, a second reference position associated with a second pattern;
setting, by a computer, a plurality of determination areas each having a predetermined range of distances from the first reference position to points in the determination area, the first pattern being located within one of the determination areas;
setting, by a computer, allowable dimensional differences for the determination areas, wherein:
each of the determination area has a corresponding allowable dimensional difference,
each of the allowable dimensional differences has a value corresponding to the predetermined range of distances of the corresponding determination area, and
the value of the allowable dimensional difference for a determination area located further away from the first reference position is larger than the value of the allowable dimensional difference for a determination area located closer to the first reference position; and
determining, by a computer, whether the second pattern has a pattern shape identical with the first pattern, based on whether a dimensional difference between a dimension of the first pattern and a corresponding dimension of the second pattern is less than or equal to the value of the allowable dimensional difference of the determination area within which the first pattern is located.

2. The method according to claim 1, wherein
a hot spot having a possibility to be a pattern formation failure higher than a predetermined value when being pattern-transferred onto a substrate is registered, and
the first pattern is set to the registered hot spot.

3. The method according to claim 1, wherein
a clean pattern having a possibility to be a pattern formation failure lower than a predetermined value when being pattern-transferred onto a substrate is registered, and
the first pattern is set to the registered clean pattern.

4. The method according to claim 1, wherein the allowable dimensional differences are set based on a maximum dimensional variation amount from an ideal value at the first reference position of a first on-substrate pattern formed on a substrate when the first pattern is transferred onto the substrate.

5. The method according to claim 1, wherein the allowable dimensional differences are set based on a minimum pattern dimension of the second pattern.

6. The method according to claim 1, wherein each of the first pattern and the second pattern is included in a design pattern.

7. The method according to claim 6, wherein the first reference position is a position of a minimum dimension on the design pattern.

8. A method of verifying a pattern shape, the method comprising:
setting, by a computer, as a point-of-interest position, a first reference position associated with a first pattern;
setting, by a computer, as a determination reference position, a second reference position associated with a second pattern;
setting, by a computer, a plurality of determination areas each having a predetermined range of distances from the first reference position to points in the determination area, the first pattern being located within one of the determination areas;
setting, by a computer, allowable dimensional differences for the determination areas, wherein:
each of the determination area has a corresponding allowable dimensional difference,
each of the allowable dimensional differences has a value corresponding to the predetermined range of distances of the corresponding determination area, and
the value of the allowable dimensional difference for a determination area located further away from the first reference position is larger than the value of the allowable dimensional difference for a determination area located closer to the first reference position;
determining, by a computer, whether the second pattern has a pattern shape identical with the first pattern, based on whether a dimensional difference between a dimension of the first pattern and a corresponding dimension of the second pattern is less than or equal to the value of the allowable dimensional difference of the determination area within which the first pattern is located;
calculating, by a computer, a shape of an on-substrate pattern formed on a substrate when the second pattern is transferred onto the substrate;
determining, by a computer, whether calculated on-substrate pattern has a desired shape; and
calculating, by a computer, the shape of the on-substrate pattern for the second pattern if the second pattern is determined not to have a patter shape identical with the first pattern and setting an identical on-substrate pattern for the second pattern if the second pattern is determined to have a pattern shape identical with the first pattern.

9. The method according to claim 8, wherein
a hot spot having a possibility to be a pattern formation failure higher than a predetermined value when being pattern-transferred onto a substrate is registered, and
the first pattern is set to the registered hot spot.

10. The method according to claim 8, wherein
a clean pattern having a possibility to be a pattern formation failure lower than a predetermined value when being pattern-transferred onto a substrate is registered, and
the first pattern is set to the registered clean pattern.

11. The method according to claim 8, wherein the allowable dimensional differences are set based on a maximum dimensional variation amount from an ideal value at the first reference position of a first on-substrate pattern formed on the substrate when the first pattern is transferred onto the substrate.

12. The method according to claim 8, wherein the allowable dimensional differences are set based on a minimum pattern dimension of the second pattern.

13. The method according to claim 8, wherein each of the first pattern and the second pattern is included in a design pattern.

14. The method according to claim 13, wherein the first reference position is a position of a minimum dimension on the design pattern.

15. A method of correcting a pattern, the method comprising:
setting, by a computer, as a point-of-interest position, a first reference position associated with a first pattern;

setting, by a computer, as a determination reference position, a second reference position associated with a second pattern;
setting, by a computer, a plurality of determination areas each having a predetermined range of distances from the first reference position to points in the determination area, the first pattern being located within one of the determination areas;
setting, by a computer, allowable dimensional differences for the determination areas, wherein:
  each of the determination area has a corresponding allowable dimensional difference,
  each of the allowable dimensional differences has a value corresponding to the predetermined range of distances of the corresponding determination area, and
  the value of the allowable dimensional difference for a determination area located further away from the first reference position is larger than the value of the allowable dimensional difference for a determination area located closer to the first reference position;
determining, by a computer, whether the second pattern has a pattern shape identical with the first pattern, based on whether a dimensional difference between a dimension of the first pattern and a corresponding dimension of the second pattern is less than or equal to the value of the allowable dimensional difference of the determination area within which the first pattern is located;
generating, by a computer, a mask pattern of a mask used when forming the second patter on a substrate by correcting the second pattern; and
generating, by a computer, the mask pattern for the second pattern if the second pattern is determined not to have a pattern shape identical with the first pattern and setting an identical mask patter for the second pattern if the second pattern is determined to have a pattern shape identical with the first pattern.

16. The method according to claim 15, wherein
a hot spot having a possibility to be a pattern formation failure higher than a predetermined value when being pattern-transferred onto a substrate is registered, and
the first pattern is set to the registered hot spot.

17. The method according to claim 15, wherein
a clean pattern having a possibility to be a pattern formation failure lower than a predetermined value when being pattern-transferred onto a substrate is registered, and
the first pattern is set to the registered clean pattern.

* * * * *